United States Patent [19]
Orr

[11] Patent Number: 5,979,442
[45] Date of Patent: Nov. 9, 1999

[54] EMERGENCY BREATHING DEVICE, AND METHODS OF CONSTRUCTING AND UTILIZING SAME

[76] Inventor: Rodney J. Orr, 3937 W. Maple, Wixom, Mich. 48393

[21] Appl. No.: 08/291,719

[22] Filed: Aug. 17, 1994

[51] Int. Cl.[6] .............................. A61M 16/00; A62B 7/00
[52] U.S. Cl. ............................... 128/204.18; 128/205.15; 128/204.28; 128/200.24
[58] Field of Search ..................... 128/200.24, 202.13, 128/204.18, 204.28; 40/538, 540, 554, 555

[56] References Cited

U.S. PATENT DOCUMENTS

| | | | |
|---|---|---|---|
| 1,848,951 | 3/1932 | Haynes | 40/555 |
| 2,177,204 | 10/1939 | Buzick et al. | 40/554 |
| 2,262,040 | 11/1941 | Pell | 40/555 |
| 2,550,954 | 5/1951 | Benedict | 40/538 |
| 2,680,317 | 6/1954 | Lewis | 40/534 |
| 2,831,607 | 4/1958 | Berndt | 128/204.18 |
| 2,855,712 | 10/1958 | Diletto | 40/538 |
| 3,483,887 | 12/1969 | Warncke et al. | 128/204.28 |
| 4,078,561 | 3/1978 | Hanson . | |
| 4,440,163 | 4/1984 | Spergel | 128/205.13 |
| 4,440,164 | 4/1984 | Werjefelt | 128/202.13 |
| 4,637,387 | 1/1987 | Hall | 128/205.24 |
| 4,710,756 | 12/1987 | Thornburg et al. | 128/206.27 |
| 4,726,365 | 2/1988 | Jablonski | 128/202.13 |
| 4,840,171 | 6/1989 | Rohling et al. | 128/206.27 |
| 4,905,684 | 3/1990 | Heffer | 128/202.13 |
| 4,996,982 | 3/1991 | Williamson | 128/205.24 |
| 5,113,854 | 5/1992 | Dosch et al. | 128/201.25 |
| 5,239,989 | 8/1993 | Chen | 128/204.18 |
| 5,301,665 | 4/1994 | Jumpertz et al. | 128/204.18 |
| 5,429,125 | 7/1995 | Wagner et al. | 128/204.18 |

FOREIGN PATENT DOCUMENTS 2030869  4/1980  United Kingdom .............. 128/202.13

OTHER PUBLICATIONS

Primatene Mist Asthma Inhaler Operating Instructions, Whitehall Laboratories, NY pp. 1 & 2.
O.G. Printout of Abstract of 5243972, Sep. 14, 1993, pp. 817–818.

*Primary Examiner*—John G. Weiss
*Assistant Examiner*—Joseph F. Weiss, Jr.
*Attorney, Agent, or Firm*—Carrier, Blackman & Associates, P.C.; Joseph P. Carrier; William D. Blackman

[57] ABSTRACT

An emergency breathing apparatus which is adapted to be located in a wide variety of settings, comprising a container for storing air or oxygen under pressure; a mouthpiece which operatively attaches to the container opening; an actuator which is connected to the air container and the mouthpiece so that activation thereof provides fluid communication therebetween, thereby discharging the pressurized air from the container to the mouthpiece; and a picture frame member integrally connected to the mouthpiece and the actuator such that the mouthpiece, air container, and actuator are substantially unobservable from a front elevational view of the apparatus.

44 Claims, 2 Drawing Sheets

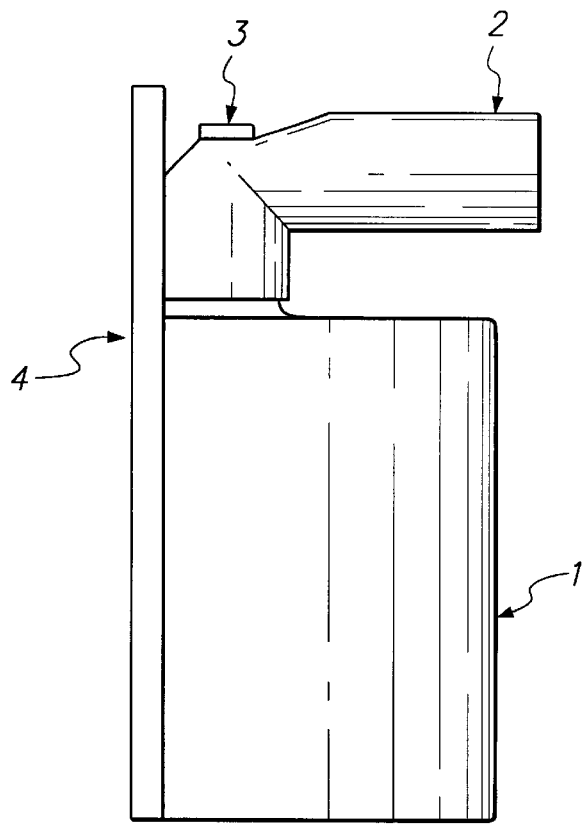
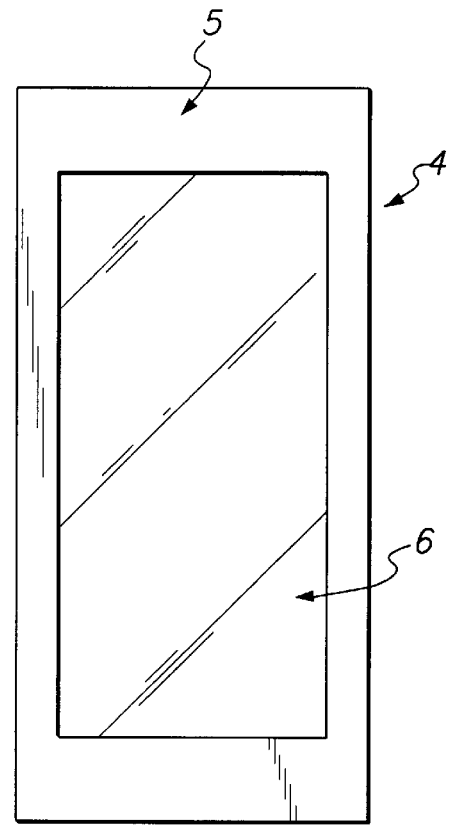
FIG. 1
FIG. 2
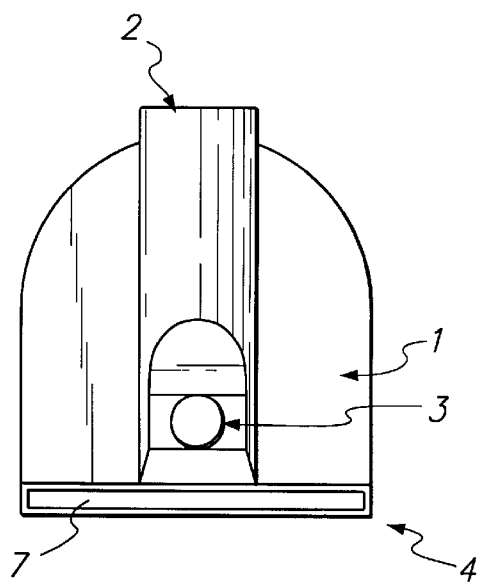
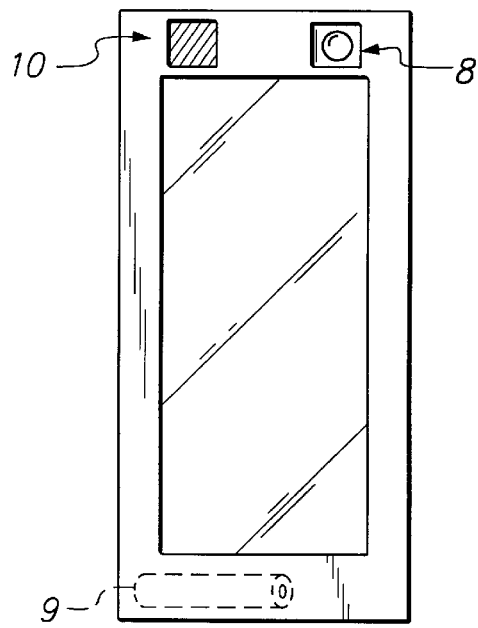
FIG. 3
FIG. 4

EMERGENCY BREATHING DEVICE, AND METHODS OF CONSTRUCTING AND UTILIZING SAME

BACKGROUND OF THE INVENTION

1. Field of Invention

This invention pertains to a device for providing air in emergency situations, and particularly to a device which may includes a decorative feature so that the device can be attractively located in any environment.

2. Description of the Relevant Art

There are known emergency breathing devices. For example, Hall U.S. Pat. No. 4,637,387 discloses a breathing apparatus having a mask operatively connected to a cylinder. Hall fails to disclose a breathing apparatus having a mouthpiece member for providing airflow to the user thereof, and a decorative front portion for aesthetically-pleasing display thereof in a variety of locations.

Williamson U.S. Pat. No. 4,996,982 discloses a portable emergency breathing apparatus having a mouthpiece, regulator, and air storage container, but fails to disclose a breathing apparatus having a decorative front portion for open, inconspicuous display thereof in a variety of settings, and means for indicating its location in darkness.

Spergel U.S. Pat. No. 4,440,163 discloses an emergency breathing apparatus which attaches to an air cylinder, but fails to disclose an emergency breathing apparatus having a decorative front portion suitable for tactful display in a variety of settings; and means for illuminating the device in darkness.

Hanson U.S. Pat. No. 4,078,561 discloses a helmet having an air supply container attached thereto. Hanson, however, fails to disclose an emergency breathing apparatus which is adapted to be conveniently yet inconspicuously displayed in a variety of settings and which includes a visual indicator for easily locating the device in darkness.

Huang U.S. Pat. No. 5,243,972 discloses a portable mask which cooperates with an oxygen tank for supplying oxygen thereto, but fails to disclose a breathing device which doubles as a home decoration when not in use, including a visual indicator for quickly identifying the location thereof in darkness.

There are known portable aerosol inhalers which provide doses of pressurized liquid medicine, such as Primatene® Mist Asthma Inhaler. Such devices, however, fail to provide air or oxygen, are not suited as a home decoration when not in use as a medicinal device, and do not include means for indicating its location.

SUMMARY OF THE INVENTION

The present invention overcomes the above-discussed limitations and shortcomings of known breathing devices and thereby satisfies a significant need for a device having a simple and effective means for supplying air or oxygen in emergency situations and being usable as a home-like functional and/or decorative device when not used as a breathing device.

According to the invention, there is provided a breathing apparatus for emergency situations, including a storage container having air or oxygen under pressure; a mouthpiece which is connected to the air container; an actuator which cooperates with the air container and the mouthpiece so as to selectively permit fluid communication therebetween; a decorative front surface for allowing the device to be conveniently located in a wide variety of settings; and audio and visual elements for easy accessibility of the device in a dark or smoke-filled environment.

In an emergency situation, the device mouthpiece is inserted into the user's mouth, and air is discharged from the pressurized air container therein by activating the actuator. The device is preferably held in place solely by the mouthpiece, thereby leaving the hands substantially free for other emergency-related acts. The activation of airflow from the device is initiated by finger or mouth movement of the actuator. Air or Oxygen is discharged from the container in a substantially continuous flow, or in bursts having predetermined duration and/or frequency.

When not in use as an emergency breathing device, the device is preferably decoratively situated in virtually any setting, by resting the device on a horizontal surface or by suspending it along a vertical surface so that its decorative front portion is in view. In a preferred embodiment, the device slidably receives a picture or photograph for display. Moreover, the device preferably includes audio and visual indicating means for quickly locating the device in a dark or smoke-filled environment.

When the pressure level within the container is low, the container may be refilled or optionally replaced by removing it from the actuator and mouthpiece assembly.

It is an object of the invention to provide an emergency breathing apparatus which is simple in design and inexpensive to manufacture.

It is another object of the invention to provide such an apparatus having means for discharging air or oxygen from a storage container simply and quickly without substantial manipulation thereof by the user's hands.

Another object of the invention is to provide a breathing apparatus having an aesthetically pleasing exterior so as to be easily accessible.

Still another object of the invention is to provide a breathing apparatus having audio and visual means for indicating the location thereof in darkness.

Other objects, advantages and salient features of the present invention will become apparent from the following detailed description, which, when taken in conjunction with the annexed drawings, discloses preferred embodiments of the present invention.

BRIEF DESCRIPTION OF THE DRAWINGS

FIG. 1 is a side elevational view of a first preferred embodiment of the present invention.

FIG. 2 is a front elevational view thereof.

FIG. 3 is a top elevational view thereof.

FIG. 4 is a front elevational view of a second preferred embodiment of the present invention.

DETAILED DESCRIPTION OF THE INVENTION

Figure 5:
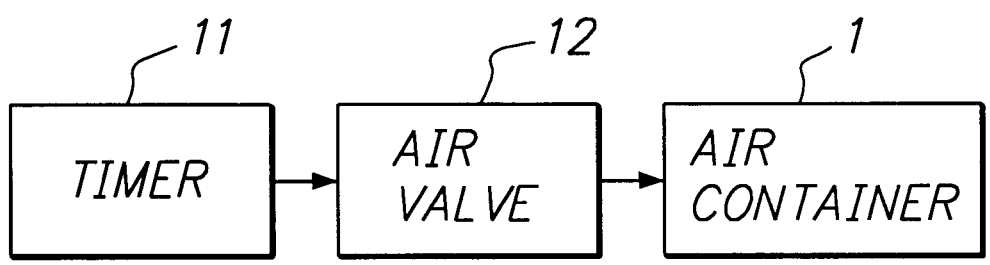
FIG. 5 is a block diagram of a preferred embodiment of the present invention.

Referring to FIGS. 1–4, there is shown an emergency breathing apparatus according to the present invention, including container 1, mouthpiece 2, actuator 3, and front section 4. The apparatus is preferably constructed from sturdy yet lightweight materials, such as molded plastic, aluminum, fiberglass, or a combination thereof. Alternatively the device is constructed from other materials. In a preferred embodiment, container 1, mouthpiece 2, actuator 3, and front section 4 are integrally connected together to form a unitary member.

Container 1 is preferably constructed so as to effectively store air or oxygen under pressure, having a port assembly for charging and/or discharging the container with air or oxygen. Such port assembly preferably but not necessarily includes a sealing valve member which is positioned within the port assembly so as to selectively control the opening of container 1.

The preferred embodiments of the present invention additionally include mouthpiece 2 and actuator 3, as shown in FIGS. 1 and 3. Mouthpiece 2 preferably but not necessarily comprises a substantially tubular portion which extends outwardly from container 1, having an opening at an end thereof for insertion within the user's mouth. A second end of mouthpiece 2 operatively attaches over the mouth portion of container 1. Alternatively, a mask is operatively attached to container 1 and adapted to fit over a user's nose and mouth region.

Actuator 3 of the present invention preferably but not necessarily includes means for selectively discharging pressurized air or oxygen from container 1 without requiring substantial manipulation of the breathing device by the user's hands. Such discharging means includes means, connected to the sealing valve member of container 1, for selectively switching the sealing valve member between a first position in which the sealing valve substantially seals the opening of container 1, and a second position in which the sealing valve allows air to pass therethrough. Such switching means, which toggles the sealing valve member of container I between the first (closed) and second (open) positions, is preferably activated by hand or mouth movements of the user, such as by activating a switch by finger applied pressure, or by blowing into or biting onto mouthpiece 2. In this way, the only manual manipulation of the breathing device necessary to discharge of gas therefrom is by a quick and simple act to initiate the discharge.

When the sealing valve member of container 1 is switched into the open position, pressurized gas is preferably discharged from container 1 having a predetermined, substantially continuous airflow which provides a sufficient air supply to the user without prematurely discharging the entire contents thereof. By way of example, the size of container 1 and the relationship between the sealing valve and the opening thereof is such that an adequate supply of air or oxygen is supplied to mouthpiece 2 for a period of several minutes.

The present invention is preferably but not necessarily adapted for use in a variety of settings, such as in a single family dwelling or a high-rise office building. Because the nature of each setting requires the breathing device to effectively provide fresh air for periods of time having different durations, the present invention is adapted for use with container 1 having a variety of sizes.

Air or oxygen is preferably but not necessarily substantially continuously discharged from container 1 until the pressure difference between container 1 and the atmosphere is substantially the same, or until the user switches the sealing valve member from the open to the closed position via finger or mouth control of actuator 3.

Alternatively, the structural relationship between actuator 3 and the sealing valve member is such that air is discharged from container 1 in bursts having predetermined duration. By way of one example, the present invention includes a battery-operated electronic means, connected to the sealing valve member, for controlling the duration of each burst and the time period therebetween for prolonged yet safe operation of the apparatus. Such electronic control means preferably but not necessarily includes a preprogrammed or programmable timer 11 for providing electrical control signals to an electromechanical sealing valve member 12 for controlling airflow from container 1 (FIG. 5). In this instance, the activation of the breathing apparatus is initiated and concluded simply by operating a switch located along the side thereof.

The present invention additionally includes means for removably attaching actuator 3 and mouthpiece 2 to container 1. Such removable attaching means allows container 1 to be either refilled or disposed of and replaced when the pressure level therein is low. In a preferred embodiment, the actuator 3 and mouthpiece 2 slide over the mouth portion of container 1. In an alternative embodiment, mouthpiece 2 threadingly engages with container 1.

The present invention further includes a functional and/or decorative front portion which may serve as an aesthetically-pleasing home-like decoration so that the invention can be conveniently located in a variety of settings. As shown in FIGS. 1–4, front portion 4 preferably but not necessarily comprises a picture frame having border member 5 and transparent portion 6. Alternatively, front portion 4 may comprise another decoration.

The frame portion of front portion 4 may have any of a variety of shapes, such as rectangular or oval-shaped, but preferably the frame is sized so that container 1, mouthpiece 2, and actuator 3 are substantially unobservable when the device is viewed along a front elevational view thereof. The decorative front portion of the device having such a frame size relative to container 1, mouthpiece 2, and actuator 3 allows the device to be located in virtually any setting fashionably and tastefully, thus improving its availability and accessibility in times of an emergency by openly maintaining the breathing device in areas where people reside.

Front portion 4 of the breathing apparatus preferably but not necessarily includes means for slidably receiving a picture or photograph. As shown in FIG. 3, front portion 4 includes elongated slot 7 defined longitudinally along front portion 4. The length and width of slot 7 are preferably but not necessarily substantially comparable to the corresponding dimensions of front portion 4, and the depth of slot 7 is preferably sized to receive a photograph or picture in a substantially fixed position therein.

According to a preferred embodiment of the present invention, front portion 4, mouthpiece 2, and actuator 3 are preferably but not necessarily integrally formed as a unitary member, such as being formed from molded plastic.

The present invention further includes means for visually indicating its location in a dark or smoke-filled environment. Such visual indicating means preferably but not necessarily comprises an outer portion of the apparatus being constructed from luminescent material so as to substantially glow in the dark following exposure to a light source. The luminescent portion of the breathing apparatus preferably includes one or more of border 5 of front portion 4, container 1, or mouthpiece 2.

Alternatively, the visual indicating means of the breathing apparatus includes light bulb 8, which is positioned along border 5 of front portion 4 (FIG. 4), or along a side portion of actuator 3. Light bulb 8 is preferably selectively activated by a switch located along a side portion of container 1. In order for light bulb 8 to function in substantially any location, light bulb 8 is preferably powered by a battery 9, which is disposed along an under portion or back portion of the breathing apparatus. In a second alternative embodiment of the present invention, the breathing apparatus includes electrical means, connected to light bulb 8, for selectively inserting within an electrical outlet so as to provide power to light bulb 8, and for suspending the breathing apparatus therealong.

The breathing apparatus of the present invention additionally includes means for generating a sound in the event of an emergency. Specifically, the sound generating means preferably but not necessarily comprises an electronic sound generator 10 which selectively automatically generates a relatively loud series of sounds, such as a series of beeping sounds. Sound generator 10 is preferably but not necessarily activated by a switch and powered by battery 9. In this way, upon activation of the sound generating means by the user, firepersons or other rescue personnel can more quickly and easily locate the user of the device. Additionally, in the event the breathing device becomes separated from the user, the user can quickly find it due to its sound generating means.

The breathing device according to the present invention preferably includes a strap which is attached to the device and is adapted to facilitate the suspension thereof when the device is in use as a emergency breathing device. The strap is preferably but not necessarily elastic so that it aids in supporting the device in the breathing position for substantially any sized user. Further, the straps allows the user to easily locate the breathing device in the event mouthpiece 2 of the device becomes dislodged from the user's mouth.

In use as a breathing device in an emergency situation, the open end of mouthpiece 2 is inserted into the user's mouth. Next, actuator 3 is activated by the user's finger or mouth, which initiates fluid communication between mouthpiece 2 and container 1 by switching the sealing valve member of container 1 into the open position. With container 1 storing air or oxygen under pressure, such establishment of fluid communication causes the gas to be discharge from container 1 into mouthpiece 2, thus discharging fresh air from container 1 into the user's respiratory system.

In one embodiment, air is discharged substantially continuously, whereas in a second embodiment air is discharged in a controlled series of periodic bursts of air. When it is no longer necessary to discharge air from the breathing apparatus, actuator 3 is deactivated, thereby switching the sealing valve member of container 1 into the closed or sealed position.

In addition, sound generating means 10 is selectively activated so as to produce a series of audio signals for indicating its location thereof in adverse conditions.

When not actively used as an emergency apparatus, the breathing device can be located in a wide variety of settings by placing a photograph or picture within slot 7 and either resting the device on a horizontal surface, hanging the device along a wall, or plugging an electrical receptacle portion thereof in an electrical outlet.

Although there have been described what are at present considered to be the preferred embodiments of the present invention, it will be understood that the invention can be embodied in other specific forms without departing from the spirit or essential characteristics thereof.

The described embodiments are, therefore, to be considered in all aspects as illustrative, and not restrictive. The scope of the invention is indicated by the appended claims rather than the foregoing description.

I claim:

1. An emergency breathing apparatus, comprising:
   means for storing air under pressure;
   a mouthpiece member;
   means, connected to said storing means and said mouthpiece member, for selectively permitting airflow from said storing means to said mouthpiece member;
   a front portion of said storing means, said mouthpiece member, and said airflow permitting means includes a decorative device;
   said air storing means, mouthpiece member and said airflow permitting means are substantially portable for suspension from a user's mouth when in use; and
   wherein said decorative device comprises a means for retaining a pictorial image.

2. A breathing apparatus as recited in claim 1, wherein:
   said air storing means, said mouthpiece member, and said decorative and/or functional device are integrally formed as a unitary member.

3. A breathing apparatus as recited in claim 1, wherein:
   said decorative and/or functional device of said apparatus is substantially flat and includes a slot defined longitudinally therewithin for slidably receiving the pictorial image.

4. A breathing apparatus as recited in claim 1, wherein:
   said pictorial retaining means substantially prevents viewing of said air storing means, said mouthpiece member, and said airflow permitting means from a front elevational view of said apparatus.

5. A breathing apparatus as recited in claim 1, including:
   means for selectively automatically audibly indicating a location of said apparatus.

6. A breathing apparatus as recited in claim 1, including:
   means, disposed along an exposed surface of said apparatus, for visually indicating the location of said apparatus in an environment having low visibility.

7. A breathing apparatus as recited in claim 6, wherein:
   said visual indicating means includes an outer surface portion of said apparatus comprising a luminescent material.

8. A breathing apparatus as recited in claim 6, wherein:
   said visual indicating means comprises a light source and a battery electrically connected thereto.

9. An emergency breathing apparatus, comprising:
   means for storing air under pressure;
   a mouthpiece member;
   means, connected to said storing means and said mouthpiece member, for selectively permitting airflow from said storing means to said mouthpiece member;
   a front portion of said storing means, said mouthpiece member, and said airflow permitting means includes a decorative device;
   said air storing means, mouthpiece member and said airflow permitting means are substantially portable for suspension from a user's mouth when in use; and
   wherein said decorative device comprises a means for retaining a pictorial image;
   said airflow permitting means selectively discharges air from said air storing means in a periodic series of bursts; and
   said airflow permitting means comprises means for controlling a duration of each of said bursts and a frequency of said periodic series of said bursts.

10. An apparatus as recited in claim 9, wherein:
    said airflow permitting means comprises a timer and an air valve member operatively associated with said timer.

11. An apparatus as recited in claim 10, wherein:

said timer is an electronic timer having means for retaining a stored value representing said predetermined frequency of said series of bursts of air and said duration of each of said bursts; and said air valve member is automatically switched between an open position in which air is discharged from said air storage means and a closed position in which air is substantially sealed within said air storage means.

12. An apparatus as recited in claim 9, further including:

means for selectively automatically audibly indicating a location of said apparatus.

13. An apparatus as recited in claim 9, further including:

means, disposed along an exposed surface of said apparatus, for visually indicating the location of said apparatus in an environment having low visibility.

14. A breathing device, comprising:

a container for maintaining air under pressure;

means for selectively discharging air contained in said container;

means, connected to said container, for orally delivering said air in said container to a user upon activation of said discharging means;

a front portion of said container, said discharging means, and said air delivering means includes a decorative front surface;

said container, said air discharging means and said air delivering means are substantially portable; and said decorative front surface comprises a frame for slidably receiving a pictorial representation.

15. A breathing device as recited in claim 14, including:

means for selectively automatically generating a series of sounds, each of said sounds being of predetermined duration and increased volume.

16. A breathing device as recited in claim 15, including:

means for visually indicating a location of said device in darkness, said visual indicating means including said frame being comprised of luminous material.

17. A breathing device as recited in claim 14, wherein:

said discharging means, said air delivering means, and said decorative front surface are integrally connected so as to form a unitary member.

18. A breathing device as recited in claim 14, including:

means for visually indicating a location of said device in an environment having low visibility.

19. A breathing device as recited in claim 14, wherein:

said front device substantially conceals viewing of said container, said discharge means, and said air delivering means from a front elevational view of said device.

20. A device as recited in claim 14, wherein:

said frame includes a slot defined therethrough for receiving a pictorial representation.

21. An emergency breathing apparatus, comprising:

means for storing pressurized gas for breathing;

a mouthpiece operatively connected to said storing means;

means, connected to said storing means, for selectively discharging air from said storing means to said mouthpiece in response to initiation of said discharging means by a user of said apparatus;

means for providing a location of said apparatus in darkness;

wherein said gas storing means, said mouthpiece and said air discharging means are substantially portable and substantially sized so as to suspend from a user's mouth when in use, means for decorating a front portion of said apparatus so as to substantially obstruct viewing of said storing means, said mouthpiece and said discharging means from a front elevational view.

22. An emergency breathing apparatus as recited in claim 21, wherein:

said apparatus location providing means includes a visual indicating means; and said visual indicating means includes an outer surface of said device comprising luminescent material.

23. An emergency breathing apparatus, comprising:

first means for providing air to a user in an emergency situation;

second means for a decorative and/or functional purpose;

said first and said second means are substantially portable;

a predetermined portion of said first means includes said second means; and said predetermined portion of said first means which includes said second means comprises a decorative front portion which serves as an aesthetically-pleasing home-like decoration so that said emergency breathing apparatus can be conveniently located in a variety of settings.

24. An emergency breathing apparatus according to claims 23, wherein:

said second means includes means for visually indicating the location of said emergency breathing apparatus in darkness.

25. An emergency breathing apparatus according to claim 24, wherein:

said second means includes means for audibly indicating the location of said emergency breathing apparatus.

26. An emergency breathing apparatus according to claim 25, wherein:

said second means includes a frame for slidably receiving a pictorial representation.

27. An emergency breathing apparatus according to claim 24, wherein:

said second means includes a frame for slidably receiving a pictorial representation.

28. An emergency breathing apparatus according to claim 24, wherein:

said visual indicating means comprises said front portion being a luminescent material.

29. An emergency breathing apparatus according to claim 23, wherein:

said second means includes means for audibly indicating the location of said emergency breathing apparatus.

30. An emergency breathing apparatus according to claim 29, wherein:

said second means includes a frame for slidably receiving a pictorial representation.

31. An emergency breathing apparatus according to claim 23, wherein:

said second means includes a frame for slidably receiving a pictorial representation.

32. An emergency breathing apparatus according to claim 31, wherein:

said frame includes a slot defined therealong for slidably receiving the pictorial representation.

33. An emergency breathing device, comprising:

means for storing air under pressure;

a mouthpiece member;

means, connected to said storing means and said mouthpiece member, for selectively permitting airflow from said storing means to said mouthpiece member;

a front portion of said storing means, said mouthpiece member, and said airflow permitting means includes a decorative device;

said air storing means, mouthpiece member and said airflow permitting means are substantially portable for suspension from a user's mouth when in use; and wherein said decorative and/or functional device comprises a means for retaining a pictorial image;

said airflow permitting means discharges air from said air storage means in a periodic series of bursts, each of said bursts being of a predetermined duration.

34. A device as recited in claim 33 wherein:

said airflow permitting means includes means for discharging air from said air storage means so that a frequency of said periodic series of bursts of air is predetermined.

35. A device as recited in claim 34, wherein:

said airflow permitting means includes an electronic timer having means for retaining a stored value representing said predetermined frequency of said series of bursts of air and said duration of each of said bursts, and an air valve member which is operatively associated with said electronic timer so that said air valve member is automatically switched between an open position in which air is discharged from said air storage means and a closed position in which air is substantially sealed within said air storage means.

36. An apparatus as recited in claim 33, further including:

means for selectively automatically audibly indicating a location of said apparatus.

37. An apparatus as recited in claim 33, further including:

means, disposed along an exposed surface of said apparatus, for visually indicating the location of said apparatus in an environment having low visibility.

38. An emergency breathing apparatus, comprising:

first means for providing air to a user in an emergency situation;

second means for a decorative purpose;

said first and said second means are substantially portable;

a predetermined portion of said first means includes said second means;

said predetermined portion of said first means which includes said second means comprises a decorative front portion which serves as an aesthetically-pleasing home-like decoration so that said emergency breathing apparatus can be conveniently located in a variety of settings; and means for automatically controlling said first means so that air is substantially provided to the user in a series of bursts of air having a predetermined frequency and a predetermined duration for each of said burst of air.

39. An emergency breathing apparatus according to claim 38, wherein:

said automatic controlling means comprises an electronic timer and an air valve member operatively associated with said electronic timer.

40. An apparatus as recited in claim 38, wherein:

said automatically controlling means comprises a timer and an air valve member operatively associated with said timer.

41. An apparatus as recited in claim 38, wherein:

said timer is an electronic timer having means for retaining a stored value representing said predetermined frequency of said series of bursts of air and said duration of each of said bursts; and said air valve member is automatically switched between an open position in which air is discharged from said first means and a closed position in which air is substantially sealed within said first means.

42. An apparatus as recited in claim 38 further including:

means for selectively automatically audibly indicating a location of said apparatus.

43. An apparatus as recited in claim 38 further including:

means, disposed along an exposed surface of said apparatus, for visually indicating the location of said apparatus in an environment having low visibility.

44. An apparatus as recited in claim 38 wherein:

said second means includes a frame for slidably receiving a pictorial representation.

* * * * *